(12) United States Patent
Jansson et al.

(10) Patent No.: US 9,833,470 B2
(45) Date of Patent: *Dec. 5, 2017

(54) DIALYSIS PRECURSOR COMPOSITION

(71) Applicant: Gambro Lundia AB, Lund (SE)

(72) Inventors: Olof Jansson, Vellinge (SE); Jens Gustafsson, Malmo (SE); Torbjorn Linden, Hasslo (SE)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/066,073

(22) Filed: Mar. 10, 2016

(65) Prior Publication Data

US 2016/0184350 A1    Jun. 30, 2016

Related U.S. Application Data

(63) Continuation of application No. 14/366,623, filed as application No. PCT/EP2012/075007 on Dec. 11, 2012, now Pat. No. 9,314,480.

(60) Provisional application No. 61/578,249, filed on Dec. 21, 2011.

(30) Foreign Application Priority Data

Dec. 21, 2011  (SE) ........................... 1151234

(51) Int. Cl.
| | | |
|---|---|---|
| A61K 33/14 | (2006.01) |
| A61K 31/194 | (2006.01) |
| A61K 31/7004 | (2006.01) |
| A61M 1/14 | (2006.01) |
| A61K 33/00 | (2006.01) |
| A61K 33/06 | (2006.01) |
| A61K 9/08 | (2006.01) |
| A61M 1/16 | (2006.01) |

(52) U.S. Cl.
CPC .............. A61K 33/14 (2013.01); A61K 9/08 (2013.01); A61K 31/194 (2013.01); A61K 31/7004 (2013.01); A61K 33/00 (2013.01); A61K 33/06 (2013.01); A61M 1/14 (2013.01); A61M 1/1654 (2013.01)

(58) Field of Classification Search
CPC .. A61K 33/14; A61K 31/194; A61K 31/7004; A61K 33/00; A61K 33/06; A61M 1/14
See application file for complete search history.

(56) References Cited

U.S. PATENT DOCUMENTS

| | | | |
|---|---|---|---|
| 3,560,380 A | 2/1971 | Stade | |
| 3,742,100 A * | 6/1973 | Boyum | B01J 2/04 264/13 |
| 4,636,412 A | 1/1987 | Field | |
| 4,756,838 A | 7/1988 | Veltman | |
| 6,610,206 B1 | 8/2003 | Callan et al. | |
| 9,029,333 B2 | 5/2015 | Sugiyama et al. | |
| 2004/0019313 A1 | 1/2004 | Childers et al. | |
| 2004/0057885 A1 | 3/2004 | Taylor | |
| 2004/0060865 A1 | 4/2004 | Callan et al. | |
| 2007/0087212 A1 | 4/2007 | Iyengar et al. | |
| 2007/0231395 A1 | 10/2007 | Kai | |
| 2008/0015487 A1 | 1/2008 | Szamosfalvi et al. | |
| 2009/0306002 A1 | 12/2009 | Nakanishi et al. | |
| 2010/0120702 A1 | 5/2010 | Sugiyama et al. | |
| 2011/0172583 A1 | 7/2011 | Callan et al. | |
| 2012/0291875 A1 | 11/2012 | Shah et al. | |

FOREIGN PATENT DOCUMENTS

| | | |
|---|---|---|
| CN | 1938058 A1 | 3/2007 |
| EP | 0 034 916 A1 | 9/1981 |
| EP | 3399918 | 11/1990 |
| EP | 0 417 478 A1 | 3/1991 |
| EP | 0 602 014 A1 | 6/1994 |
| EP | 0 602 921 A1 | 6/1994 |
| EP | 1 059 083 A1 | 12/2000 |
| EP | 1 101 483 A2 | 5/2001 |
| EP | 1 192 961 A2 | 4/2002 |
| EP | 1 714 657 A1 | 10/2006 |
| EP | 1 731 183 A1 | 12/2006 |
| EP | 1 834 652 A1 | 9/2007 |
| EP | 2 119 438 A1 | 11/2009 |
| EP | 2 123 270 A1 | 11/2009 |
| EP | 2 151 247 A1 | 2/2010 |
| EP | 2 286 820 A1 | 2/2011 |
| FR | 2766797 A1 | 2/1999 |

(Continued)

OTHER PUBLICATIONS

Ahmad et al., "Dialysate Made From Dry Chemicals Using Citric Acid Increases Dialysis Dose," American Journal of Kidney Diseases, vol. 35, No. 3 (March), 2000: pp. 493-499.

Gabutti et al., "Citrate- vs. acetate-based dialysate in bicarbonate haemodialysis: consequences on haemodynamics, coagulation, acid-base status, and electrolytes," BMC Nephrology 2009, 10:7.

Gärtner, Heinz, "Developments in barrier films," Symposium "Sperrschichtfolien [Barrier films]" on Jun. 30/Jul. 1, 2004, Würzburg, Germany.

Nilsson, "Citrate vs. Acetate in Bicarbonate-Based Dialysis Fluid—What Does it Mean Clinically?" White Paper Gambro Lundia AB, Mar. 2012. 5 pages.

(Continued)

Primary Examiner — Anoop K Singh
Assistant Examiner — Doan T Phan
(74) Attorney, Agent, or Firm — K&L Gates LLP

(57) ABSTRACT

A dialysis acid precursor assembly including: a dry dialysis acid precursor composition including sodium chloride, a dry acid and a magnesium chloride 4.5-hydrate (MgCl2.4.5H2O), a calcium salt and at least one of a potassium salt, calcium salt and an anhydrous glucose, and a moisture-resistant container having a water vapor transmission rate less than 0.2 g/m2/d at 38° C./90% RH, wherein the dry dialysis acid precursor composition is sealed in the container.

11 Claims, No Drawings

(56) References Cited

FOREIGN PATENT DOCUMENTS

| | | | |
|---|---|---|---|
| JP | H04-257522 A | 9/1992 |
| JP | H10-87478 A | 4/1998 |
| JP | 2003-104869 A | 4/2003 |
| JP | 2005-206572 A | 8/2005 |
| RU | 2006103497 A | 8/2007 |
| TW | 200911287 A | 3/2009 |
| WO | 92/11046 A1 | 7/1992 |
| WO | 00/57935 A1 | 10/2000 |
| WO | 01/21233 A1 | 3/2001 |
| WO | 03/043680 A1 | 5/2003 |
| WO | 2005/002599 A1 | 1/2005 |
| WO | 2010/055963 A1 | 5/2010 |
| WO | 2010112547 | 10/2010 |
| WO | 2010112570 | 10/2010 |
| WO | 2011/161055 A1 | 12/2011 |
| WO | 2011/161056 A2 | 12/2011 |
| WO | 2012/175353 A1 | 12/2012 |
| WO | 2012/175354 A1 | 12/2012 |
| WO | 2013/004362 A1 | 1/2013 |

OTHER PUBLICATIONS

TW200911287 Application—Incomplete Translation—p. 1 is missing.
TW200911287—Translation of Office Action—8 pages.
Ing T.S. et al., Employing L-lactic acid powder in the preparation of a dry "acid concentrate" for use in a bicarbonate-based dialysis solution-generating system: experience in hemodialysis patients, The International journal of artificial organs 1994, vol. 17, nr 2, p. 70-73.
Japanese Office Action for Japanese Application No. 2013-515839, dated Jul. 28, 2015.
Barry et al. (Basis for Using Moisture Vapor Transmission Rate Per Unit Product in the Evaluation of Moisture-Barrier Equivalence of Primary Packages for Solid Oral Dosage Forms, 2004).
CurTec article (http://www.pharmaceutical-networking.com/moisture-resistant-packaging/) 2015.
Nikhil Mehrotra (Masters Theses): A Study of Water Vapor Transmission Rate of Blister Packs by USP Standard and Continuous Gravimetric Protocol 2010.
International Search Report cited in PCT/EP2012/060969 dated Oct. 2, 2012.
Sigma-Aldrich Product Spedification form for Calcium Chloride; downloaded Mar. 15, 2016.
Norner AS download showing WVTR calculation for: FEP layer (1-mm); downloaded Feb. 13, 2015.
Norner AS download showing WVTR calculation for: PMMA layer (1-mm); downloaded Feb. 14, 2015.
Norner AS download showing WVTR calculation for: PTFE layer (1-mm); downloaded Feb. 14, 2015.
Norner AS download showing WVTR calculation for: PTFE-PTFE dual-layer (1-mm); downloaded Feb. 14, 2015.
Norner AS download showing WVTR calculation for: PTFE layer (2-mm); downloaded Feb. 14, 2015.
Norner AS download showing WVTR calculation for: PVDC layer (1-mm); downloaded Feb. 13, 2015.
Norner AS download showing WVTR calculation for: PTFE-PMMA dual-layer (1-mm); downloaded Feb. 14, 2015.
Oracle Packaging; data for aluminum foil; downloaded Feb. 16, 2015.
International Search Report cited in PCT/EP2012/060971 dated Aug. 21, 2012.
Magnesium chloride 4.5 hydrate, European Pharmacopoeia 7.3 Jan. 2012.
International Preliminary Report on Patentability for International Application No. PCT/EP2012/075008, dated Jun. 24, 2014.
International Search Report for International Application No. PCT/EP2012/075008, dated Mar. 6, 2013.
Written Opinion of the International Searching Authority for International Application No. PCT/EP2012/075008, dated Mar. 6, 2013.
Search Report for related International Patent Application No. PCT/EP2013/054386 dated May 23, 2013 (6 pages).
Written Opinion for related International Patent Application No. PCT/EP2013/054386 dated May 23, 2013 (5 pages).
Notice of Opposition filed in related European Patent case No. 11729087.4-1453 / 2585076 by Fresenius Medical Care AG & Co. KGaA on Dec. 3, 2015 (16 pages).
Vortrag Dr. Gartner mit dem Titel, "Entwicklungen bei Sperrschichtfolien", ("Fachtagung, Sperrschichtfolien" vom 30. Juni/1 Juli 2004 in Wurzburg) nebst eidesstattlicher Versicherung des Hernn Dietmar Hansel (reference D3 cited in Notice of Opposition filed in related European patent application No. case No. 11729087.4-1453 / 2585076 by Fresenius Medical Care AG & Co. KGaA on Dec. 3, 2015) (35 pages).
Summons to attend oral proceedings pursuant to Rule 115(1) EPC issued in related European Patent case No. 11729087.4-1453 / 2585076 on Aug. 30, 2016 (9 pages).
Observations (Experimental Data) filed in related European patent application No. case No. 11729087.4-1453 / 2585076 by Gambro Lundia AB on Aug. 5, 2016 (5 pages).
Declaration of Ola Carlsson filed in related European patent application No. case No. 11729087.4-1453 / 2585076 by Gambro Lundia AB on Aug. 5, 2016 (13 pages).
International Preliminary Report on Patentability for International Application No. PCT/EP2012/075007 dated Jun. 24, 2014.
International Search Report for International Application No. PCT/EP2012/075007 dated Mar. 6, 2013.
Written Opinion of the International Searching Authority for International Application No. PCT/EP2012/075007 dated Mar. 6, 2013.
Gambro Lundia AB's Response to Opposition filed in related European patent application No. 11729087.4 on Aug. 5, 2016.
Kipouros et al., "A Thermal Analysis of the Production of Anhydrous MgCl2," Journal of Light Metals, May 2001 (reference D4 cited in Response to Opposition filed in related European patent application No. 11729087.4 on Aug. 5, 2016).
Declaration of David Karlsson relating to film thickness, dated Jul. 29, 2016 (reference D5 cited in Response to Opposition filed in related European patent application No. 11729087.4 on Aug. 5, 2016).
Annex A (curriculum vitae) of David Karlsson Declaration (annex to reference D5 cited in Response to Opposition filed in related European patent application No. 11729087.4 on Aug. 5, 2016).
Translation Declaration signed by Don Sanderson on Jul. 22, 2016 attesting to the translation of selected paragraphs of JP 10-87478 (reference D2 cited by opponent Fresenius Medical Care), (reference D6 cited in Response to Opposition filed in related European patent application No. 11729087.4 on Aug. 5, 2016).
Experimental annex providing stability data (reference D7 cited in Response to Opposition filed in related European patent application No. 11729087.4 on Aug. 5, 2016).
English translation of Japanese Office Action issued Nov. 22, 2016 in corresponding Japanese application No. 2014-560335 (4 pages).

\* cited by examiner ns is a continuation of U.S. patent application Ser. No. 14/366,623, filed on Jun. 18, 2014, which is the U.S. National Stage of International Application No. PCT/EP2012/075007, filed Dec. 11, 2012, which designated the U.S. and claims priority to SE 1151234-0, filed Dec. 21, 2011, and U.S. Provisional Patent Application No. 61/578, 249, filed Dec. 21, 2011, the entire contents of each of which are being incorporated herein by reference.

DIALYSIS PRECURSOR COMPOSITION

PRIORITY CLAIM

This application is a continuation of U.S. patent application Ser. No. 14/366,623, filed on Jun. 18, 2014, which is the U.S. National Stage of International Application No. PCT/EP2012/075007, filed Dec. 11, 2012, which designated the U.S. and claims priority to SE 1151234-0, filed Dec. 21, 2011, and U.S. Provisional Patent Application No. 61/578, 249, filed Dec. 21, 2011, the entire contents of each of which are being incorporated herein by reference.

TECHNICAL FIELD

The present invention concerns a dialysis acid precursor composition for use during preparation of a dialysis acid concentrate solution and for further mixing with water and a bicarbonate containing concentrate into a ready-for-use dialysis solution. The present invention further concerns a method of providing a dialysis acid concentrate solution for dilution with water and a bicarbonate concentrate to produce a ready-for-use dialysis solution. Even further, the present invention concerns use of said dialysis acid precursor composition for preparation of a dialysis acid concentrate solution, for preparing a dialysis solution, an infusion solution, a replacement fluid, a rinsing solution or a priming solution.

BACKGROUND

When a person's kidney does not function properly uremia is developed. Dialysis is a well established treatment technique for uremia. Essentially, dialysis artificially replaces the functions of the kidney. There are two distinct types of dialysis; hemodialysis and peritoneal dialysis.

Hemodialysis involves withdrawing blood from the body and cleaning it in an extracorporeal blood circuit and then returning the cleansed blood to the body. The extracorporeal blood circuit includes a dialyzer which comprises a semipermeable membrane. The semipermeable membrane has a blood side and a dialysate side. Waste substances and excess fluid is removed from the blood passing on the blood side of the semipermeable membrane through the semipermeable membrane over to the dialysate side of the semipermeable membrane.

Hemodialysis may be performed in three different treatment modes; hemodialysis, hemofiltration, and hemodiafiltration. Common to all three treatment modes is that the patient is connected by a blood line to the dialysis machine, which continuously withdraws blood from the patient. The blood is then brought in contact with the blood side of the semipermeable membrane within the dialyzer in a flowing manner.

In hemodialysis, an aqueous solution called dialysis solution is brought in contact with the opposite membrane surface, the dialysate side, in a flowing manner. Waste substances (toxins) and solutes are removed/controlled mainly by diffusion. Excess fluid is removed by applying transmembrane pressure over the semipermeable membrane. Solutes and nutrients may diffuse in the opposite direction from the dialysis solution, through the semipermeable membrane and into the blood.

In hemofiltration, no dialysis solution is brought in contact with the dialysate side of the semipermeable membrane. Instead only a transmembrane pressure is applied over the semipermeable membrane thereby removing fluid and waste substances from the blood through the semipermeable membrane wall and into the dialysate side thereof (convective flow). Fluid and waste substances are then passed to drain. To replace some of the removed fluid, a correctly balanced electrolyte/buffer dialysis solution (also named infusion fluid or replacement fluid) is infused into the extracorporeal blood circuit. This infusion may be done either pre the dialyzer (pre-infusion mode) or post the dialyzer (post-infusion mode) or both.

Hemodiafiltration is a combination of hemodialysis and hemofiltration, a treatment mode that combines transport of waste substances and excess fluids through the semipermeable membrane wall by both diffusion and convection. Thus, here a dialysis solution is brought in contact with the dialysate side of the semipermeable membrane in a continuously flowing manner, and a dialysis solution (also named infusion fluid or replacement fluid) is used for infusion into the extracorporeal blood circuit in pre-infusion mode, post-infusion mode or both.

For many patients, hemodialysis is performed for 3-5 hours, three times per week. It is usually performed at a dialysis centre, although home dialysis is also possible. When home dialysis is performed the patients is free to perform dialysis more frequently and also in more gentle treatments with longer duration, i.e. 4-8 hours per treatment and 5-7 treatments per week. The dose and duration may be adjusted to each patient's demands and needs.

In the case of patients suffering from acute renal insufficiency, a continuous treatment, throughout a major portion of the entire day for up to several weeks, a continuous renal replacement therapy (CRRT), or intermittent renal replacement therapy (IRRT) is the indicated treatment depending on the patient's status. Also here the removal of waste substances and excess fluid from the patient is effected by any or a combination of the treatment modes hemodialysis, hemofiltration and hemodiafiltration.

In a peritoneal dialysis treatment a hypertonic dialysis solution is infused into the peritoneal cavity of the patient. In this treatment solutes and water is exchanged in the capillary vessels of a patient's peritoneal membrane with said hypertonic dialysis solution. The principle of this method is diffusion of solutes transferred according to the concentration gradient and water migration due to the osmotic differences over the peritoneal membrane.

The dialysis solutions used in all the above dialysis techniques contain mainly electrolytes like sodium, magnesium, calcium, potassium, an acid/base buffer system buffers and optionally glucose or a glucose-like compound. All the components in dialysis solutions are selected to control the levels of electrolytes and the acid-base equilibrium within the blood and to remove waste materials from the blood.

Dialysis solutions are today prepared from different types of concentrates. It may be liquid concentrates of different degree of concentration, where the acid/electrolyte part is separated from the buffer part. It may be provided in highly concentrated volumes of 1-8 L in bags for bedside use, or in more diluted concentrated volumes of 5-20 L in canisters, which still are for bedside use. Concentrates may also be prepared in central tanks in volumes of 300-1000 L.

When using bicarbonate as a buffer component in the dialysis solution, bicarbonate is often provided as a dry concentrate for on-line-preparation of saturated bicarbonate containing concentrate. The saturated bicarbonate containing concentrate is thereafter mixed with an acid/electrolyte concentrate and further diluted with purified water to produce the on-line prepared dialysis solution.

Dialysis solutions have improved in quality over the years, and the availability of concentrated precursor compositions for further dilution and mixing with other components into a ready-for-use dialysis solution have decreased the costs and improved the environmental issues.

One way to further limit the costs and improve the environmental issues would be to provide a dialysis precursor composition in which all components are dry. However, having all components as dry components adds new problems.

Firstly, dry acid and bicarbonate powder are not compatible. When a small amount of humidity is present, bicarbonate will break down to carbon dioxide.

Secondly, magnesium chloride and calcium chloride mixed with bicarbonate will provide areas were the solubility product of calcium carbonate and/or magnesium carbonate will be exceeded, which would cause precipitation thereof when water is added during preparation of a concentrate or a dialysis solution.

Thirdly, even if bicarbonate is excluded to a separate cartridge, still problems would be experienced. E.g. caking and lump formation of the different components will render the dissolution thereof more difficult or even impossible when preparing the ready-for-use dialysis solution.

Fourthly, if glucose is present, a discoloration of the precursor, and later on, the ready-for-use dialysis solution would arise as a result of glucose degradation products, which should be avoided due to toxicity and limits set by authority regulations, e.g. European Pharmacopeia.

All the problems above are due to the presence of humidity within the dry precursor compositions.

In prior art this has been solved by preparing granulates of the different components and creating different layers of the different components within each granulate, like disclosed in EP0567452 or EP1714657.

However, this still may give rise to interactions between the different layers, and it is also a time-consuming matter of providing a completely and properly dissolved granulate for the preparation of the ready-for-use dialysis solution. Further, it is difficult to ensure proper composition and concentration of the different components both within the granulate and thus also within the finally prepared ready-for-use dialysis solution.

SUMMARY

One object of the present invention is to provide a dialysis precursor composition which show further improved stability, limited chemical degradation and increased shelf life.

Another object of the present invention is to provide a dialysis precursor composition which give rise to further cost savings and further improved environmental benefits.

The present invention concerns a dialysis acid precursor composition for use during preparation of a dialysis acid concentrate solution and for further mixing with water and a bicarbonate containing concentrate into a ready-for-use dialysis solution. Said dialysis acid precursor composition consists of powder components comprising sodium chloride, at least one dry acid and at least one magnesium salt, and optionally potassium salt, calcium salt, and glucose. According to the invention said optional glucose is present as anhydrous component in said dialysis acid precursor composition, and said at least one magnesium salt is present as magnesium chloride 4.5-hydrate ($MgCl_2 \cdot 4.5H_2O$). Further, said dialysis acid precursor composition is sealed in a moisture-resistant container with a water vapour transmission rate less than 0.2 $g/m^2/d$ at 38° C./90% RH.

The present invention further concerns a method of providing a dialysis acid concentrate solution for dilution with water and a bicarbonate containing concentrate to produce a ready-for-use dialysis solution. According to the invention this method comprises:

(a) providing a dialysis precursor composition comprising sodium chloride, at least one dry acid, and at least one magnesium salt, optionally potassium salt, calcium salt, and glucose, wherein said optional glucose, i.e. if glucose is present, is present as anhydrous component in said dialysis acid precursor composition and wherein said at least one magnesium salt is present as magnesium chloride 4.5-hydrate ($MgCl_2 \cdot 4.5H_2O$), (b) providing said dialysis precursor composition in a sealed, moisture-resistant container with a water vapour transmission rate less than 0.2 $g/m^2/d$ at 38° C./90% RH, and (c) adding a prescribed volume of water to said dialysis precursor composition in said container and mixing thereof, thereby providing said dialysis acid concentrate as a solution.

The present invention further concerns use of said dialysis acid precursor composition for preparing a dialysis acid concentrate solution.

Finally, the present invention concerns use of said dialysis acid precursor composition for preparing a dialysis solution, an infusion solution, a replacement solution, a rinsing solution, or a priming solution.

Other embodiments of the present invention are evident from the description below and the dependent claims.

DETAILED DESCRIPTION

A wide variety of different combinations and partitions of dry powder components of normal dialysis solutions like potassium chloride, magnesium chloride, calcium chloride, glucose, sodium chloride, sodium bicarbonate, dry acids like citric acid, glucono-δ-lactone, etc. were prepared and put in a forced stability study. Matters like caking, lump formation, discoloration and dissolution rate were investigated after 1 month, 4 months and 10 months storage time.

It was identified that, as expected, sodium bicarbonate needs to be separated from the other components due to carbon dioxide formation, calcium carbonate precipitation, and magnesium carbonate precipitation. However, when combining the remaining components of a normal dialysis solution, the six crystalline water (hexahydrate) attached to magnesium chloride caused problems with caking and lump formation within the powder compositions and discoloration of glucose (if present). By replacing magnesium chloride hexahydrate with magnesium chloride 4.5-hydrate, the powder composition unexpectedly remained stable, free flowing and no discoloration evolved. Thus, in order to make sure that a stable composition is provided the container material used for storing the composition should be moisture-resistant and not allow passage of an amount equal to or above the amount which equals the difference in crystalline water between hexahydrate and 4.5-hydrate magnesium salt. This is achieved with a container material having a water vapour transmission rate less than 0.2 $g/m^2/d$ at 38° C./90% RH.

In another embodiment said container material has a water vapour transmission rate less than 0.1 $g/m^2/d$ at 38° C./90% RH.

In another embodiment said container material as ha water vapour transmission rate of more than 0.05 $g/m^2/d$ at 38° C./90% RH.

In another embodiment said container material has a water vapour transmission rate between 0.05-0.2 $g/m^2/d$ at 38° C./90% RH.

In even another embodiment said container material has a water vapour transmission rate between 0.05-0.1 $g/m^2/d$ at 38° C./90% RH.

According to the invention said dialysis acid precursor composition consists of powder components comprising sodium chloride, at least one dry acid and at least one magnesium salt, and optionally potassium salt, calcium salt, and glucose, wherein said optional glucose is present as anhydrous component in said dialysis acid precursor composition and wherein said at least one magnesium salt is present as magnesium chloride 4.5-hydrate ($MgCl_2.4.5H_2O$) within the moisture-resistant container.

In other embodiments of the present invention said at least one dry acid is selected from the group comprising lactic acid, citric acid, gluconic acid, glucono-δ-lactone, N-acetyl cystein and α-lipoic acid. Thus, a combination of dry acids may be used within said dialysis acid precursor composition, and by providing a combination of different dry acids, other functions and effects, in addition to said acidic function, may be provided, like for instance antioxidative effects (as with citric acid, gluconic acid, glucono-δ-lactone, N-acetyl cystein and α-lipoic acid), anticoagulation effects (as with citric acid) and so forth.

In other embodiments, in which calcium salt is present, said calcium salt in said dialysis acid precursor composition, is at least one selected from the group comprising calcium chloride dihydrate, calcium chloride monohydrate, anhydrous calcium chloride, calcium gluconate, calcium citrate, calcium lactate, and calcium .alpha.-ketoglutarate. Thus, also here a combination of different calcium salts may be used.

In another embodiment, said calcium salt is calcium chloride dihydrate ($CaCl_2.2H_2O$).

In one embodiment said dialysis precursor composition is provided in a specific amount and is configured to be mixed with a prescribed volume of water within said moisture-resistant container to provide a dialysis acid concentrate solution. Thus, said moisture-resistant container is configured to receive and dispense solutions up to said prescribed volume.

In one embodiment said prescribed volume may be within the range of from 1 to 8 L.

In another embodiment said prescribed volume may be within the range of from 5-20 L.

In even another embodiment said prescribed volume may be within the range of 300-1000 L.

Further, in one embodiment said dialysis acid concentrate solution is configured and provided to be diluted within the range of 1:30 to 1:50 with water and a bicarbonate concentrate.

The present invention further concerns a method of providing a dialysis acid concentrate solution. Said dialysis acid concentrate solution is further intended to be mixed with additional water and a bicarbonate concentrate to produce a ready-for-use dialysis solution. According to the invention said method comprises (a) providing a dialysis precursor composition comprising sodium chloride, at least one dry acid, and at least one magnesium salt, optionally potassium salt, calcium salt, and glucose, wherein said optional glucose is present as anhydrous component in said dialysis acid precursor composition, and wherein said at least one magnesium salt is present as magnesium chloride 4.5-hydrate ($MgCl_2.4.5H_2O$) (b) providing said dialysis precursor composition in a sealed, moisture-resistant container with a water vapour transmission rate less than 0.2 $g/m^2/d$ at 38° C./90% RH, and (c) adding a prescribed volume of water to said dialysis precursor composition in said container and mixing thereof, thereby providing said dialysis acid concentrate as a solution.

Sodium chloride is provided in such a quantity in said moisture-resistant container that a concentration within the range of 2.55-5.5 M sodium chloride is provided in the dialysis acid concentrate solution when a prescribed volume of water has entered into said moisture-resistant container.

Said dry acid is provided in such a quantity in said moisture-resistant container that a concentration within the range of 60-200 mEq/L $H^+$ (acid) is provided in the dialysis acid concentrate solution when a prescribed volume of water has entered into said moisture-resistant container.

Further, said at least one magnesium salt is provided in such a quantity in said moisture-resistant container that a concentration within the range of 7.5-50 mM magnesium ions is provided in the dialysis acid concentrate solution when a prescribed volume of water has entered into said moisture-resistant container.

If present, said calcium salt is provided in such a quantity in said moisture-resistant container that a concentration within the range of 30-125 mM calcium ions is provided in the dialysis acid concentrate solution when a prescribed volume of water has entered into said moisture-resistant container.

If present, potassium salt is provided in such a quantity in said moisture-resistant container that a concentration within the range of 0-200 mM potassium ions is provided in the dialysis acid concentrate solution when a prescribed volume of water has entered into said moisture-resistant container.

If present, glucose is provided in such a quantity in said moisture-resistant container that a concentration within the range of 0-100 g/L is provided in the dialysis acid concentrate solution when a prescribed volume of water has entered into said moisture-resistant container.

In one embodiment said dry dialysis acid precursor composition comprises the different components in such an amount that, when said dry dialysis acid precursor composition has been dissolved and mixed with water and bicarbonate, it provides a ready-for-use dialysis solution comprising from about 130-150 mM of sodium ions, from about 0 to 4 mM of potassium ions, from about 1-2.5 mM of calcium ions, from about 0.25 to 1 mM of magnesium ions, from about 0 to 2 g/l glucose, from about 85 to 134 mM chloride ions, from about 2 to 4 mEq/L acid, and from about 20 to 40 mEq/L bicarbonate ions.

Thus, the present invention provides a prepackaged container with a dry dialysis acid precursor composition for use during preparation of a dialysis acid concentrate solution and for mixing with water and a bicarbonate containing concentrate into a ready-for-use dialysis solution, wherein said dialysis acid precursor composition consists of powder components comprising sodium chloride, at least one dry acid and at least one magnesium salt. Optionally said dialysis acid precursor composition further comprises potassium salts, calcium salts, and glucose. According to the invention said at least one magnesium salt is present as magnesium chloride 4.5-hydrate ($MgCl_2.4.5H_2O$) in said dialysis acid precursor composition and said dialysis acid precursor composition is sealed in a moisture-proof container with a water vapour transmission rate less than 0.2 $g/m^2/d$ at 38° C./90% RH.

When using magnesium chloride 4.5-hydrate ($MgCl_2.4.5H_2O$) powder in a dry dialysis acid precursor composition, the dry dialysis acid precursor composition unexpectedly remain stable, lump free and without glucose degradation.

EXAMPLES

By way of example, and not limitation, the following examples identify a variety of dialysis acid precursor compositions pursuant to embodiments of the present invention.

In examples 1-4, the tables show the content of dialysis acid precursor compositions for dilution 1:35. The prescribed volume of each dialysis acid concentrate solution (DACS in tables below) is 5.714 L, and the final volume of each ready-for-use dialysis solution (RFUDS in tables below) is 200 L.

Example 1

| Ingredient | Amount (g) | Conc in DACS (mM) | Conc in RFUDS (mM) |
|---|---|---|---|
| Sodium chloride | 1169 | 3500 | 100 |
| Potassium chloride | 29.81 | 70 | 2 |
| Magnesium chloride 4.5-hydrate | 17.63 | 17.5 | 0.5 |
| Calcium chloride dihydrate | 44.10 | 52.5 | 1.5 |
| Citric acid | 38.42 | 35 | 1 |
| Glucose anhydrous | 200 | 194.4 | 5.55 |

Example 2

| Ingredient | Amount (g) | Conc in DACS (mM) | Conc in RFUDS (mM) |
|---|---|---|---|
| Sodium chloride | 1169 | 3500 | 100 |
| Potassium chloride | 29.81 | 70 | 2 |
| Magnesium chloride 4.5-hydrate | 17.63 | 17.5 | 0.5 |
| Calcium gluconate | 129.1 | 52.5 | 1.5 |
| Citric acid | 38.42 | 35 | 1 |
| Glucose anhydrous | 200 | 194.4 | 5.55 |

Example 3

| Ingredient | Amount (g) | Conc in DACS (mM) | Conc in RFUDS (mM) |
|---|---|---|---|
| Sodium chloride | 1169 | 3500 | 100 |
| Potassium chloride | 29.81 | 70 | 2 |
| Magnesium chloride 4.5-hydrate | 17.63 | 17.5 | 0.5 |
| Calcium chloride dihydrate | 44.10 | 52.5 | 1.5 |
| Glucono-delta-lactone | 35.63 | 35 | 1 |
| Citric acid | 30.73 | 28 | 0.8 |
| Glucose anhydrous | 200 | 194.4 | 5.55 |

Example 4

| Ingredient | Amount (g) | Conc in DACS (mM) | Conc in RFUDS (mM) |
|---|---|---|---|
| Sodium chloride | 1169 | 3500 | 100 |
| Potassium chloride | 29.81 | 70 | 2 |
| Magnesium chloride 4.5-hydrate | 17.63 | 17.5 | 0.5 |
| Calcium chloride anhydrous | 33.30 | 52.5 | 1.5 |
| Glucono-delta-lactone | 142.5 | 140 | 4 |
| Glucose anhydrous | 200 | 194.4 | 5.55 |

In example 5-9, the tables show the content of a dry acid precursor composition for dilution 1:45. The prescribed volume of each dialysis acid concentrate solution (DACS in tables below) is 5.33 L, and the final volume of each ready-for-use dialysis solution (RFUDS in tables below) is 240 L.

Example 5

| Ingredient | Amount (g) | Conc in DACS (mM) | Conc in RFUDS (mM) |
|---|---|---|---|
| Sodium chloride | 1401.7 | 4500 | 100 |
| Potassium chloride | 71.57 | 180 | 4 |
| Magnesium chloride 4.5-hydrate | 21.16 | 22.5 | 0.5 |
| Calcium chloride dihydrate | 61.74 | 78.75 | 1.75 |
| Citric acid | 46.10 | 45 | 1 |
| Glucose anhydrous | 240 | 250 | 5.55 |

Example 6

| Ingredient | Amount (g) | Conc in DACS (mM) | Conc in RFUDS (mM) |
|---|---|---|---|
| Sodium chloride | 1401.7 | 4500 | 100 |
| Potassium chloride | 53.68 | 135 | 3 |
| Magnesium chloride 4.5-hydrate | 21.16 | 22.5 | 0.5 |
| Calcium gluconate | 129.12 | 56.25 | 1.25 |
| Citric acid | 46.10 | 45 | 1 |

Example 7

| Ingredient | Amount (g) | Conc in DACS (mM) | Conc in RFUDS (mM) |
|---|---|---|---|
| Sodium chloride | 1401.7 | 4500 | 100 |
| Magnesium chloride 4.5-hydrate | 21.16 | 22.5 | 0.5 |
| Calcium gluconate | 180.77 | 78.75 | 1.75 |
| Citric acid | 46.10 | 45 | 1 |
| Glucose anhydrous | 240 | 250 | 5.55 |

Example 8

| Ingredient | Amount (g) | Conc in DACS (mM) | Conc in RFUDS (mM) |
|---|---|---|---|
| Sodium chloride | 1401.7 | 4500 | 100 |
| Potassium chloride | 35.78 | 90 | 2 |

-continued

| Ingredient | Amount (g) | Conc in DACS (mM) | Conc in RFUDS (mM) |
|---|---|---|---|
| Magnesium chloride 4.5-hydrate | 21.16 | 22.5 | 0.5 |
| Calcium chloride dihydrate | 52.92 | 67.5 | 1.5 |
| Glucono-delta-lactone | 42.75 | 45 | 1 |
| Citric acid | 36.88 | 36 | 0.8 |
| Glucose anhydrous | 240 | 250 | 5.55 |

Example 9

| Ingredient | Amount (g) | Conc in DACS (mM) | Conc in RFUDS (mM) |
|---|---|---|---|
| Sodium chloride | 1401.7 | 4500 | 100 |
| Potassium chloride | 71.57 | 180 | 4 |
| Magnesium chloride 4.5-hydrate | 21.16 | 22.5 | 0.5 |
| Calcium chloride anhydrous | 26.64 | 45 | 1 |
| Citric acid | 46.10 | 45 | 1 |
| Glucose anhydrous | 240 | 250 | 5.55 |

Tests

Tests has been performed to study the stability of different dry powder compositions, both according to embodiments of the present invention as well as comparisons. Parameters like caking, lumping and discoloration were evaluated.

Methods

Plastic films were welded into bags with 1 compartment.

Composition 1

The amount of powder components of potassium chloride, magnesium chloride 4.5-hydrate, calcium chloride dihydrate, anhydrous glucose, citric acid, and sodium chloride necessary to produce 230 L of dialysis fluid were filled into the plastic bags, with a water vapor transmission rate of 0.11 g/m$^2$/d at 38° C./90% RH. The bags were sealed and incubated in 30° C., 65% RH, and in 40° C., 75% RH, respectively.

Composition 2

The amount of powder components of potassium chloride, magnesium chloride 4.5-hydrate, anhydrous calcium chloride, anhydrous glucose, citric acid, and sodium chloride necessary to produce 230 L of dialysis fluid were filled into the plastic bags, with a water vapor transmission rate of 0.11 g/m$^2$/d at 38° C./90% RH. The bags were sealed and incubated in 30° C., 65% RH, and in 40° C., 75% RH, respectively.

Comparison Composition 3

The amount of powder components of potassium chloride, anhydrous magnesium chloride, calcium chloride dihydrate, anhydrous glucose, citric acid, and sodium chloride necessary to produce 230 L of dialysis fluid were filled into the plastic bags, with a water vapor transmission rate of 2.7 g/m$^2$/d at 38° C./90% RH. The bags were sealed and incubated in 30° C., 65% RH, and in 40° C., 75% RH, respectively.

Comparison Composition 4

The amount of powder components of potassium chloride, magnesium chloride hexahydrate, calcium chloride dihydrate, anhydrous glucose, citric acid, and sodium chloride necessary to produce 230 L of dialysis fluid were filled into glass bottles, thus with no water vapor transmission. The bags were sealed and incubated in 30° C., 65% RH, and in 40° C., 75% RH, respectively.

Comparison Composition 5

The amount of powder components of potassium chloride, anhydrous magnesium chloride, anhydrous calcium chloride, anhydrous glucose, citric acid, and sodium chloride necessary to produce 230 L of dialysis fluid were filled into the plastic bags, with a water vapor transmission rate of 2.7 g/m$^2$/d at 38° C./90% RH. The bags were sealed and incubated in 40° C., 75% RH.

Results

Compositions 1 and 2 have proven to stay stable for at least one year, while comparison compositions 3 and 4 failed due to formation of brown lumps after less than 1 month. Comparison composition 5 also failed due to formation of brown lumps after 1 to 3 months.

While the invention has been described in connection with what is presently considered to be the most practical embodiments, it is to be understood that the invention is not to be limited to the disclosed embodiments, but on the contrary, is intended to cover various modifications and equivalents included within the spirit and the scope of the appended claims.

The invention claimed is:

1. A dialysis acid precursor composition for use in preparation of a dialysis acid concentrate solution and for mixing with water and a bicarbonate containing concentrate into a ready-for-use dialysis solution, the dialysis acid precursor composition comprising:
   powder components comprising sodium chloride, at least one dry acid, an anhydrous calcium chloride powder, and magnesium chloride 4.5-hydrate (MgCl$_2$.4.5H$_2$O), wherein the anhydrous calcium chloride powder is in a quantity such that a concentration of 30-125 mM calcium ions is provided in the dialysis acid concentrate solution.

2. The dialysis precursor composition of claim 1, wherein the at least one dry acid is selected from the group consisting of lactic acid, citric acid, gluconic acid, glucono-δ-lactone, N-acetyl cysteine, and α-lipoic acid.

3. The dialysis precursor composition of claim 1, wherein the dialysis precursor composition is prepared to be mixed with a prescribed volume of water to form a dialysis acid concentrate solution.

4. A method comprising adding water to the dialysis acid precursor composition of claim 1 to form a dialysis acid concentrate solution.

5. A method comprising adding water to the dialysis acid precursor composition of claim 1 to form a dialysis acid concentrate solution, and diluting the dialysis acid concentrate solution with water to form a solution selected from the group consisting of a dialysis solution, an infusion solution, a replacement solution, a rinsing solution and a priming solution.

6. The dialysis acid precursor composition of claim 1, wherein the powder components comprise at least one of a potassium salt and an anhydrous glucose.

7. A method of providing a dialysis acid concentrate solution for dilution with water and a bicarbonate containing concentrate to produce a ready-for-use dialysis solution, the method comprising:
   providing a dialysis precursor comprising sodium chloride, at least one dry acid, an anhydrous calcium chloride powder, and magnesium chloride 4.5-hydrate (MgCl$_2$.4.5H$_2$O); and
   adding a prescribed volume of water to the dialysis precursor composition and mixing thereof, thereby providing the dialysis acid concentrate solution, wherein the anhydrous calcium chloride powder is in a quantity such that a concentration of 30-125 mM calcium ions is provided in the dialysis acid concentrate solution.

8. The method of claim 7, wherein the dialysis acid precursor composition comprises at least one of a potassium salt and an anhydrous glucose.

9. The method of claim 7, wherein the ready-for-use dialysis solution is selected from the group consisting of a dialysis solution, an infusion solution, a replacement solution, a rinsing solution, and a priming solution.

10. The method of claim 7, wherein the at least one dry acid is selected from the group consisting of lactic acid, citric acid, gluconic acid, glucono-δ-lactone, N-acetyl cysteine, and α-lipoic acid.

11. The method of claim 7 comprising mixing the dialysis acid concentrate solution with a sodium containing concentrate and a bicarbonate containing concentrate to produce the ready-for-use dialysis solution.

\* \* \* \* \*